US011065030B2

(12) United States Patent
Sahadevan et al.

(10) Patent No.: US 11,065,030 B2
(45) Date of Patent: Jul. 20, 2021

(54) ATHERECTOMY SYSTEM

(71) Applicant: BOSTON SCIENTIFIC LIMITED, Hamilton (BM)

(72) Inventors: Joshin Sahadevan, Bangalore (IN); Ganesh Rajendran, Bangalore (IN)

(73) Assignee: BOSTON SCIENTIFIC LIMITED

( * ) Notice: Subject to any disclaimer, the term of this patent is extended or adjusted under 35 U.S.C. 154(b) by 229 days.

(21) Appl. No.: 16/236,173

(22) Filed: Dec. 28, 2018

(65) Prior Publication Data
US 2019/0201052 A1 Jul. 4, 2019

Related U.S. Application Data

(60) Provisional application No. 62/613,023, filed on Jan. 2, 2018.

(51) Int. Cl.
*A61B 17/3207* (2006.01)
*A61B 1/00* (2006.01)
*A61B 17/00* (2006.01)

(52) U.S. Cl.
CPC .... *A61B 17/320758* (2013.01); *A61B 1/0016* (2013.01); *A61B 1/00133* (2013.01);
(Continued)

(58) Field of Classification Search
CPC ........ A61B 17/320758; A61B 17/3207; A61B 17/320725; A61B 17/320783; A61B 17/320016; A61B 17/32003; A61B 2017/00389; A61B 2017/00477; A61B 1/00113; A61B 1/0016; H01H 13/02; H01H 13/04; H01H 13/06; H01H 13/08;
(Continued)

(56) References Cited

U.S. PATENT DOCUMENTS 5,217,478 A * 6/1993 Rexroth ........... A61B 17/32002
606/172
5,314,407 A * 5/1994 Auth .............. A61B 17/320758
604/22

(Continued)

FOREIGN PATENT DOCUMENTS

WO 2011106606 A1 9/2011

OTHER PUBLICATIONS

International Search Report and Written Opinion dated Apr. 2, 2019 for International Application No. PCTUS2018068029.

*Primary Examiner* — Kathleen S Holwerda
(74) *Attorney, Agent, or Firm* — Seager, Tufte & Wickhem, LLP

(57) ABSTRACT

Medical systems and methods for making and using medical systems are disclosed. Example medical systems may include an atherectomy system configured to engage and remove plaque from walls in vessels of a vascular system. The atherectomy system may include a drive shaft, a rotational tip coupled to an end of the drive shaft, a drive mechanism coupled to the drive shaft to rotate the rotational tip, a control unit configured to control operation of the drive mechanism, and a knob assembly configured to facilitate longitudinal movement of the drive shaft, the rotational tip, and/or the drive mechanism. In some cases, the knob assembly may be configured to initiate adjustment of a mode of the drive mechanism in response to actuation of an actuator in the knob assembly.

20 Claims, 6 Drawing Sheets

(52) U.S. Cl.
CPC .............. *A61B 2017/00389* (2013.01); *A61B 2017/00477* (2013.01)

(58) Field of Classification Search
CPC ........ H01H 13/10; H01H 13/12; H01H 13/14; H01H 13/15; H01H 13/18; H01H 23/146; H01H 23/148; H01H 23/164; H01H 23/08; H01H 23/12; H01H 2300/014; H01H 19/14; H01H 19/60; H01H 3/12; H01H 3/122; H01H 25/006; H01H 25/065; H01H 2025/004; H01H 1/18; H01H 1/36
USPC .................................................. 606/159, 180
See application file for complete search history.

(56) References Cited

U.S. PATENT DOCUMENTS

| | | | |
|---|---|---|---|
| 5,779,722 A * | 7/1998 | Shturman | A61B 17/320758 |
| | | | 606/159 |
| 7,584,022 B2 | 9/2009 | Shturman et al. | |
| 2011/0087254 A1 | 4/2011 | Welty | |
| 2011/0213391 A1* | 9/2011 | Rivers | A61B 17/320758 |
| | | | 606/159 |
| 2015/0142027 A1 | 5/2015 | Rydberg et al. | |
| 2017/0290603 A1* | 10/2017 | Piippo Svendsen | |
| | | | A61B 17/320758 |

* cited by examiner

US 11,065,030 B2

ATHERECTOMY SYSTEM

CROSS-REFERENCE TO RELATED APPLICATIONS

This application claims the benefit of priority under 35 U.S.C. § 119 of U.S. Provisional Application No. 62/613,023, filed Jan. 2, 2018, the entire disclosure of which is hereby incorporated by reference.

TECHNICAL FIELD

The present disclosure pertains to medical devices, and methods for manufacturing and using medical devices. More particularly, the present disclosure pertains to rotational medical devices, methods, and systems, including those with drive mechanisms and actuation controls.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

BRIEF SUMMARY

This disclosure provides, design, material, manufacturing method, and use alternatives for medical devices and systems. In a first aspect, an atherectomy device may include a housing, a drive mechanism positioned within the housing and configured to couple to an elongate member and rotate the elongate member upon actuation, a knob assembly in communication with the drive mechanism and operably accessible from exterior the housing, the knob assembly may be configured to longitudinally translate to adjust an axial position of the drive mechanism, and be actuated to selectively adjust the drive mechanism between an on mode and an off mode.

In addition or alternative and in a second aspect, the knob assembly may be configured to longitudinally translate along a fixed longitudinal distance and be releasably engaged with the housing to fix the drive mechanism at a location along the fixed longitudinal distance.

In addition or alternative and in a third aspect, the knob assembly may comprise an actuator that is actuated to selectively adjust the drive mechanism between the on mode and the off mode.

In addition or alternative and in a fourth aspect, the knob assembly may comprise a switch configured to facilitate adjusting the drive mechanism between the on mode and the off mode, and an actuator configured to engage the switch in response to being actuated, the actuator engages the switch to adjust the drive mechanism between the on mode and the off mode.

In addition or alternative and in a fifth aspect, the knob assembly may comprise a slide adaptor coupled to the drive mechanism, a knob body coupled to the slide adaptor and configured to releasably engage the housing to fix the drive mechanism at an axial location along the housing, and an actuator configured to be actuated to selectively adjust the drive mechanism between the on mode and the off mode.

In addition or alternative and in a sixth aspect, the knob assembly may comprise a switch configured to axially translate with the drive mechanism and facilitate adjusting the drive mechanism between the on mode and the off mode, and wherein the actuator is configured to engage the switch in response to being actuated.

In addition or alternative and in a seventh aspect, the knob assembly may comprise a printed circuit board in electrical communication with the switch and coupled with the slide adaptor.

In addition or alternative and in an eighth aspect, the device may further comprise a control assembly configured to control power to the drive mechanism, and the knob assembly may comprise a printed circuit board in electrical communication with the switch and configured to axially translate with the drive mechanism, the printed circuit board is in electrical communication with the control assembly.

In addition or alternative and in a ninth aspect, the actuator may be coupled to the slide adaptor and configured to translate with the drive mechanism between a first axial position of the drive mechanism and a second axial position of the drive mechanism.

In addition or alternative and in a tenth aspect, the knob body may be coupled to the slide adaptor via a first connection and a second connection, the knob body may be configured to be adjusted via the second connection to selectively engage the housing and fix the drive mechanism at the axial location along the housing.

In addition or alternative and in an eleventh aspect, the drive mechanism may be a turbine.

In addition or alternative and in a twelfth aspect, a method of actuating an atherectomy device of an atherectomy system may comprise releasing a knob assembly from a releasably fixed position at a location on a predetermined path along a housing of the atherectomy device, actuating an actuator of the knob assembly to initiate an on mode of a drive mechanism in the housing of the atherectomy device, and longitudinally translating the knob assembly on the predetermined path.

In addition or alternative and in a thirteenth aspect, the method may further comprise when the drive mechanism is in the on mode, actuating the actuator of the knob assembly to initiate an off mode of the drive mechanism.

In addition or alternative and in a fourteenth aspect, the actuator may be actuated while the knob assembly is fixed at the location on the predetermined path.

In addition or alternative and in a fifteenth aspect, the actuator may be actuated while the knob assembly is released from the releasably fixed position.

In addition or alternative and in a sixteenth aspect, the method may further comprise rotating a knob body of the knob assembly until the knob body engages the housing of the atherectomy device to releasably fix the knob assembly relative to the housing.

In addition or alternative and in a seventeenth aspect, an atherectomy device may comprise a drive mechanism configured to rotate an elongate member securable to the drive mechanism, a knob assembly comprising a slide adaptor secured relative to the drive mechanism, a knob body adjustably secured to the slide adaptor, and an actuator adjustably secured to the slide adaptor, and wherein the knob assembly may be configured to longitudinally translate with the drive mechanism and actuation of the actuator may initiate a mode of the drive mechanism.

In addition or alternative and in an eighteenth aspect, the knob assembly may comprise a switch in communication with the actuator such that actuation of the actuator adjusts the switch to initiate a mode of the drive mechanism.

In addition or alternative and in a nineteenth aspect, the knob assembly may comprise a printed circuit board coupled to the slide adaptor and in electrical communication with the switch.

In addition or alternative and in a twentieth aspect, the knob body may be adjustable between a first position that facilitates longitudinal translation of the drive mechanism and a second position that releasably fixes the drive mechanism at a longitudinal location and the actuator is actuatable to initiate a mode of the drive mechanism when the knob body is in the first position and when the knob body is in the second position.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
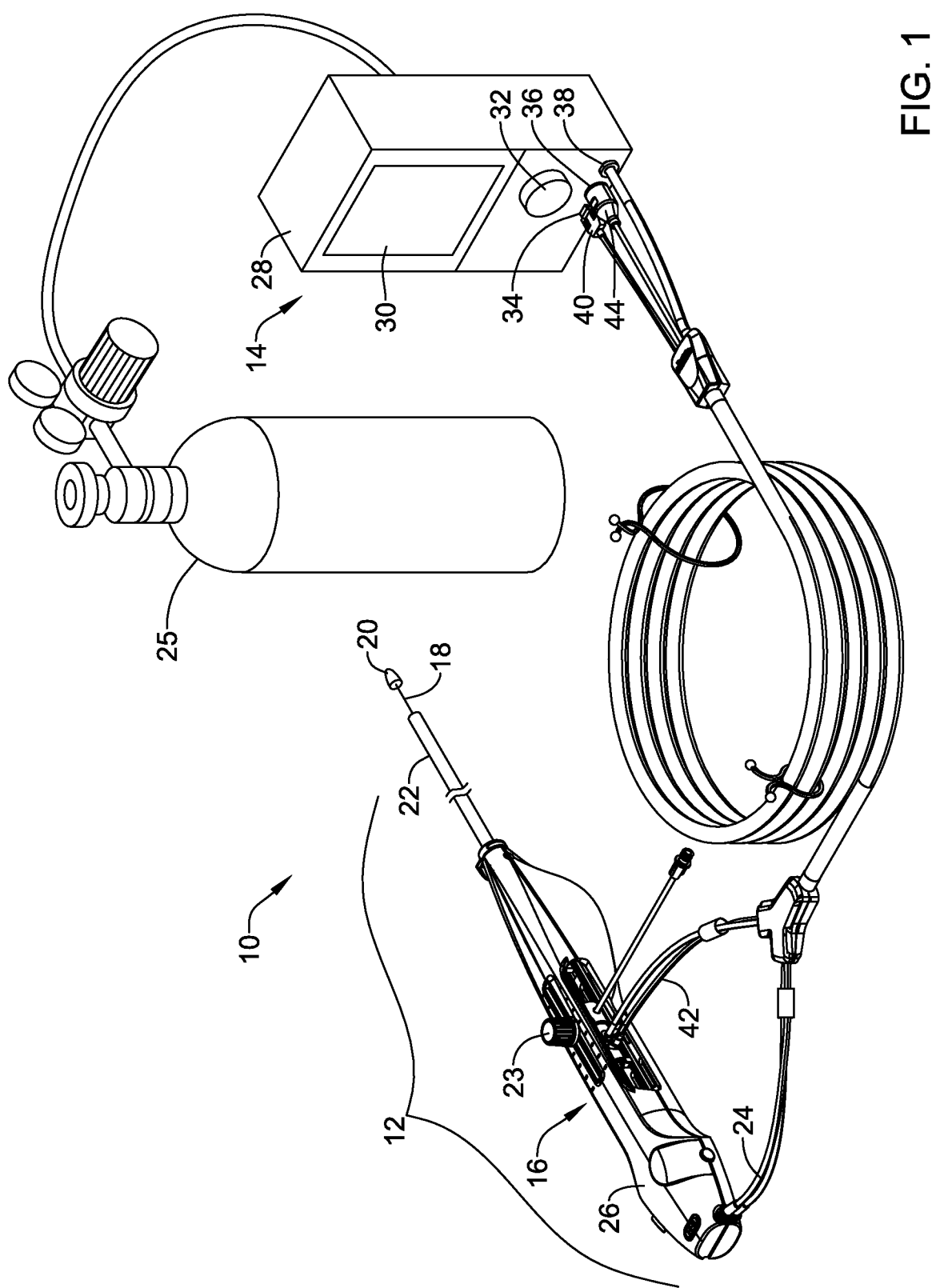
FIG. 1 is a schematic diagram of an example atherectomy system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits may restrict blood flow and can cause ischemia in a heart of a patient, vasculature of a patient's legs, a patient's carotid artery, etc. Such ischemia may lead to pain, swelling, wounds that will not heal, amputation, stroke, myocardial infarction, and/or other conditions.

Atheromatous deposits may have widely varying properties, with some deposits being relatively soft and others being fibrous and/or calcified. In the latter case, the deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and/or a variety of catheter-based approaches that may rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material. In an atherectomy procedure, a device on an end of a drive shaft is used to engage and/or remove (e.g., abrade, grind, cut, shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction.

FIG. 1 depicts an atherectomy system 10. The atherectomy system 10 may include a drive assembly 12 (e.g., an atherectomy device) and a control unit 14 (e.g., a controller or control console). Although the drive assembly 12 and the control unit 14 are depicted in FIG. 1 as separate components of the atherectomy system 10, the features of the control unit 14 may be incorporated into the drive assembly 12.

The drive assembly 12 may include, among other elements, an advancer assembly 16, a drive shaft 18 (e.g., a flexible drive shaft or other drive shaft), a rotational device 20 (e.g., a rotational tip or other rotational device), and an elongated member 22 having a first end (e.g., a proximal end), a second end (e.g., a distal end), and a lumen extending from the first end to the second end for receiving the drive shaft 18. In some cases, the elongated member 22 may be an elongated tubular member. The rotational device 20 may have a rough or sharp surface, such that it is configured to grind, abrade, cut, shave, etc. plaque from a vessel wall or other obstruction in a vessel when it is rotated.

The advancer assembly 16 may include an advancer knob assembly 23 and may house a drive mechanism (e.g., the drive mechanism 50 shown in FIG. 5; the drive mechanism may be a turbine, an electric motor, pneumatic motor, and/or one or more other suitable drive mechanisms) in communication with the advancer knob assembly 23 and the drive shaft 18. The advancer knob assembly 23 may be configured to translate along a longitudinal path to longitudinally advance and/or retract the drive mechanism, the drive shaft 18, and/or and the rotational device 20, secure the drive mechanism at an axial location along the longitudinal path, and/or adjust a mode of the drive mechanism.

Although the drive mechanism is described herein as being included in the advancer assembly 16, it is contemplated that the drive mechanism may be separate from, but in communication with the advancer assembly 16. In such cases, the knob assembly 23 may be utilized to advance the drive mechanism, the drive shaft 18, and/or the rotational device 20 and initiate actuation of a mode of the drive mechanism.

The drive mechanism may be coupled to the drive shaft 18 in a suitable manner including, but not limited to a weld connection, a clamping connection, an adhesive connection, a threaded connection, and/or other suitable connection configured to withstand high rotational speeds and forces. As the drive shaft 18 may rotate over a wide range of speeds (e.g., at speeds of between zero (0) rotations per minute (RPM) and 250,000 RPM or higher in a clockwise and/or counterclockwise direction), the coupling between the drive mechanism and the drive shaft 18 may be configured to withstand such rotational speed and associated forces.

In some cases, the drive mechanism may be in communication with the control unit 14. When in communication with the control unit 14, the drive mechanism may be in direct communication with the control unit (e.g., directly connected via wiring) or indirect communication (e.g., indirectly connected via multiple wiring connections and/or one or more devices). One example of indirect communication between a drive mechanism and the control unit 14 may include a drive mechanism (e.g., a turbine or pneumatic motor) powered by compressed air, where the control unit 14 may activate a compressed fluid flow from a cylinder 25 or other component to the drive mechanism (e.g., activate a valve of the control unit 14 or otherwise activate the compressed fluid flow), which may result in rotation of the drive mechanism and the drive shaft 18.

The drive shaft 18 may be formed from one or more of a variety of materials. For example, the drive shaft 18 may be formed from one or more of a variety of materials including steel, stainless steel, and/or other suitable materials.

The drive shaft 18 may have a suitable diameter and/or length for traversing vasculature of a patient. In some cases, the drive shaft 18 may have a diameter in a range from about 0.030 centimeters (cm) or smaller to about 0.150 cm or larger and a working length in a range from about ten (10) cm or shorter to about three hundred (300) cm or longer. Alternatively, the drive shaft 18 may have a different suitable diameter and/or a different suitable length.

The rotational device 20 may have an outer perimeter which is equal to or larger than a distal diameter of the drive shaft 18 and the elongated member 22. The rotational device 20 may have a symmetric design so that it penetrates equally well in both rotational directions, but this is not required and the rotational device 20 may be configured to penetrate in only one direction. The diameter of the drive shaft 18 may depend on the dimension of the lumen of the elongated member 22 and/or one or more other factors.

The rotational device 20 may be coupled to the drive shaft 18. Where the drive shaft 18 has a first end portion (e.g., a proximal end portion) and a second end portion (e.g., a distal end portion), the rotational device 20 may be coupled to the drive shaft 18 at or near the second end portion. In some cases, the rotational device 20 may be located at or adjacent a terminal end of the second end portion of the drive shaft 18.

The rotational device 20 may be coupled to the drive shaft 18 in any manner. For example, the rotational device 20 may be coupled to the drive shaft 18 with an adhesive connection, a threaded connection, a weld connection, a clamping connection, and/or other suitable connection configured to withstand high rotational speeds and forces. Similar to as discussed above with respect to the connection between the drive shaft 18 and the drive mechanism, as the drive shaft 18 and/or the rotational device 20 may rotate at speeds between zero (0) RPM and 250,000 RPM or higher in a clockwise direction, a counter clockwise direction, or both a clockwise direction and a counter clockwise direction, the coupling between the drive shaft 18 and the rotational device 20 may be configured to withstand such rotational speeds and associated forces.

The drive assembly 12 and the control unit 14 may be in communication and may be located in or may have a same housing and/or located in or have separate housings (e.g., an advancer assembly housing 26 and a control unit housing 28, respectively, or other housings). Whether in the same housing or in separate housings, the drive assembly 12 and the control unit 14 may be in communication through a wired (e.g., via one or more electrical lines 24) and/or a wireless connection. Wired connections may be made via one or more communication protocols including, but not limited to, USB, Ethernet, SPI, UART, HDMI, and/or any other suitable common or proprietary wired protocol, as desired. Wireless connections may be made via one or more communication protocols including, but not limited to, cellular communication, ZigBee, Bluetooth, WiFi, IrDA, dedicated short range communication (DSRC), EnOcean, and/or any other suitable common or proprietary wireless protocol, as desired.

Although not necessarily shown in FIG. 1, the drive assembly 12 may include and/or enclose one or more operational features in addition to those discussed above and/or as alternatives to those discussed above. For example, among other features, the drive assembly 12 may include control buttons, rubber feet, control electronics, drive circuitry, etc.

The control unit 14, which may be separate from the drive assembly 12 (e.g., as shown in FIG. 1) or may be included in the drive assembly 12, may include several features. For example, as shown in FIG. 1, the control unit 14 may include a display 30 and a control knob 32 (e.g., a drive mechanism speed (e.g., RPM or other speed) adjustment knob or other control knob). Additionally or alternatively, the control unit 14 may include one or more other features for controlling the drive mechanism and/or other features of the drive assembly 12 (e.g., one or more drive mechanism states) including, but not limited to, a processor, memory, input/output devices, a speaker, volume control buttons, on/off power supply switch, drive mechanism mode activation switch, a timer, a clock, and/or one or more other features.

The display 30 may be or may include any suitable type of display panel using any suitable display panel technology. For example, the display 30 may include one or more of the following types of display panels: Eidophor, Electroluminescent display (ELD), Electronic paper (E Ink, Gyricon), Light emitting diode display (LED), Cathode ray tube (CRT) (Monoscope), Liquid-crystal display (LCD) (TFT, LED, Blue Phase, IPS), Plasma display panel (PDP) (ALiS), Digital Light Processing (DLP), Liquid crystal on silicon (LCoS), Organic light-emitting diode (OLED) (AMOLED), Organic light-emitting transistor (OLET), Surface-conduction electron-emitter display (SED), Field emission display (FED), Laser TV (Quantum dot, Liquid crystal), MEMS display (IMoD, TMOS, DMS), Quantum dot display (QD-LED), Ferro liquid display (FLD), Thick-film dielectric electroluminescent technology (TDEL), Telescopic pixel display (TPD), Laser Phosphor Display (LPD), or other type of display panel. The display 30 may include a touch sensitive screen for receiving input, but this is not required.

The control knob 32 may be any suitable type of control knob. As depicted in FIG. 1, the control knob 32 may be a physical control knob that is adjusted (e.g., rotated or otherwise translated) to adjust a control feature (e.g., speed of rotation of the drive mechanism or other control feature). Alternatively or in addition, the control knob 32 may be physical buttons, a virtual control knob that may be adjusted by interacting with a touch sensitive surface, and/or other suitable component configured to be adjusted to adjust a control feature.

As depicted in FIG. 1, the control unit 14 may include one or more ports including, but not limited to, a fiber optic port 34, an electrical port 36, a fluid port 38, and/or one or more other ports. The fiber optic port 34 may be configured to receive a fiber optic connector 40 of a fiber optic line 42, where the fiber optic line 42 may be connected to and/or may be part of a position sensor configured to optically sense a position of the drive mechanism. Additionally or alternatively, other types of position sensors (e.g., tachometers) may be utilized that have different types of connections to the control unit 14. The electrical port 36 may be configured to receive an electrical connector 44 of the electrical line 24, where the electrical line 24 may be connected to and/or may be part of control electronics at the drive assembly 12. In some cases, the electrical line 24 may be directly connected to a main PCB of the drive assembly 12 and may be utilized to power an electrical assembly of the drive assembly 12. The fluid port 38 may be configured to receive a fluid line connector 46 of a fluid line 48, where the fluid line 48 may be in communication with the drive mechanism to power the drive mechanism. In instances when the drive mechanism is an electrical motor or a non-pneumatic drive mechanism, the fluid port 38, the fluid line connector 46, and/or the fluid line 48 may be omitted, but this is not required.

Figure 2:
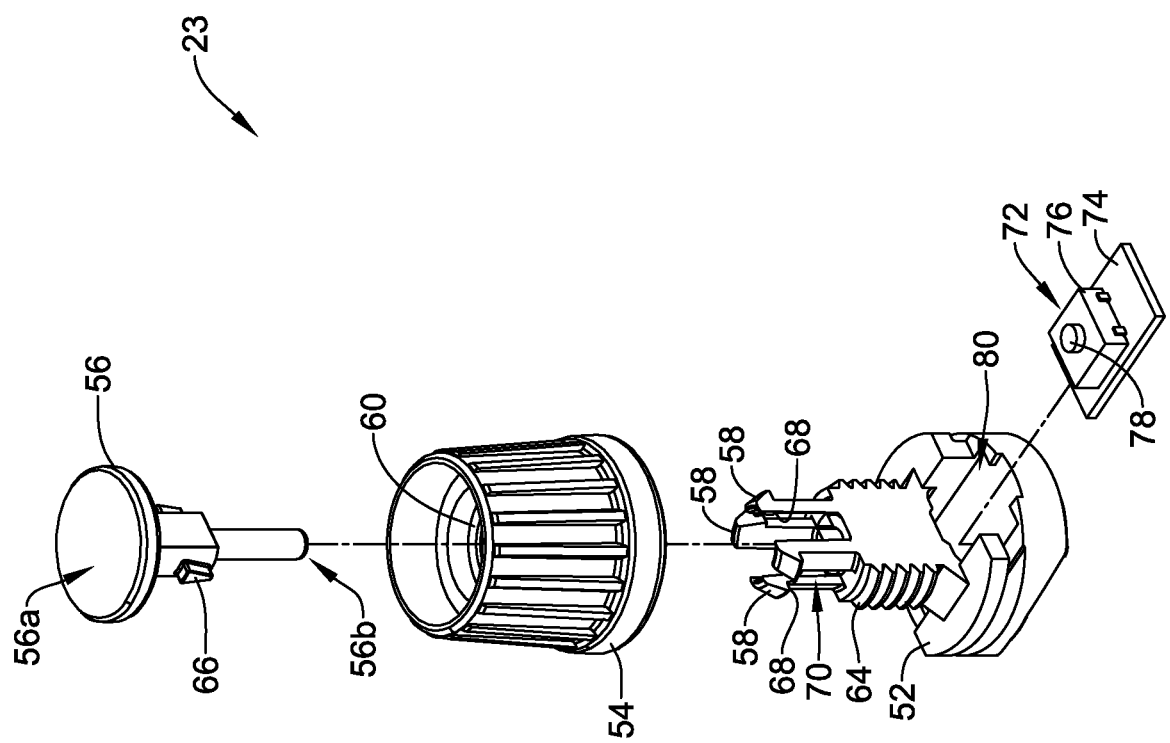
FIG. 2 is a schematic exploded view of an example knob assembly for an atherectomy system.

FIG. 2 depicts a schematic exploded perspective view of the knob assembly 23. In some cases, the knob assembly 23 may include a slide adaptor 52, a knob body 54, an actuator 56 and/or one or more other components. The knob body 54 of the knob assembly 23 may receive the slide adaptor 52 and may be configured to be secured to or relative to the slide adaptor 52. Each component (e.g., the slide adaptor 52, the knob body 54, the actuator 56, and/or other component) of the knob assembly 23 may be unitarily formed or formed from two or more component parts fitted together in a suitable manner.

The knob body 54 may be secured to or relative to the slide adaptor 52 in a suitable manner. For example, the knob body 54 may be secured to or relative to the slide adaptor 52 via a snap connection, a threaded connection, a keyed fit connection, a friction fit connection, and/or other suitable connection. In the example knob assembly 23 depicted in FIG. 2, the knob body 54 may be connectable to the slide adaptor 52 via a first connection and a second connection, however, only a single connection may be utilized or more than two connections may be utilized.

In some cases, the first connection may be configured to facilitate securing the knob body 54 relative to the slide adaptor 52 while allowing the knob body 54 to axially translate along an axis and/or rotate about the axis relative to the slide adaptor 52. In some cases, the first connection may be a snap connection between the knob body 54 and the slide adaptor 52 and/or other connection that allows axial translation and/or rotation of the knob body 54 relative to the slide adaptor 52 after connecting the knob body 54 and the slide adaptor 52. When the first connection is a snap connection, the slide adaptor 52 may include one or more engagement elements (e.g., four engagement elements 58, such as flexible and/or resilient prongs, as shown in FIG. 2 or other suitable engagement elements) that may be configured to engage one or more shoulders of the knob body 54 (e.g., shoulder 60 as shown in FIG. 2 or other suitable shoulder(s)) and allow the knob body 54 to translate relative to the slide adaptor 52.

Figure 4:
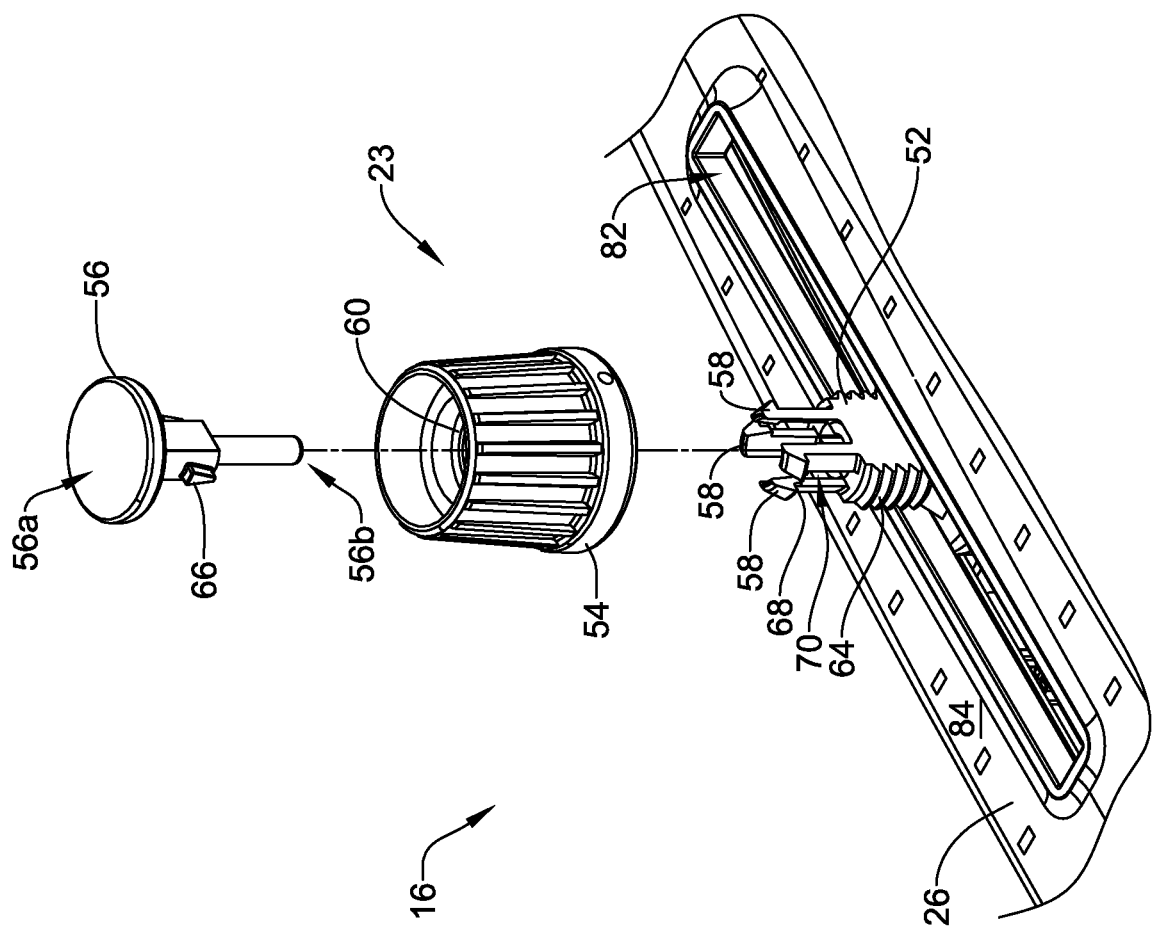
FIG. 4 is a schematic perspective view of a portion of an example advancer assembly with a knob assembly in an exploded configuration.
Figure 5:
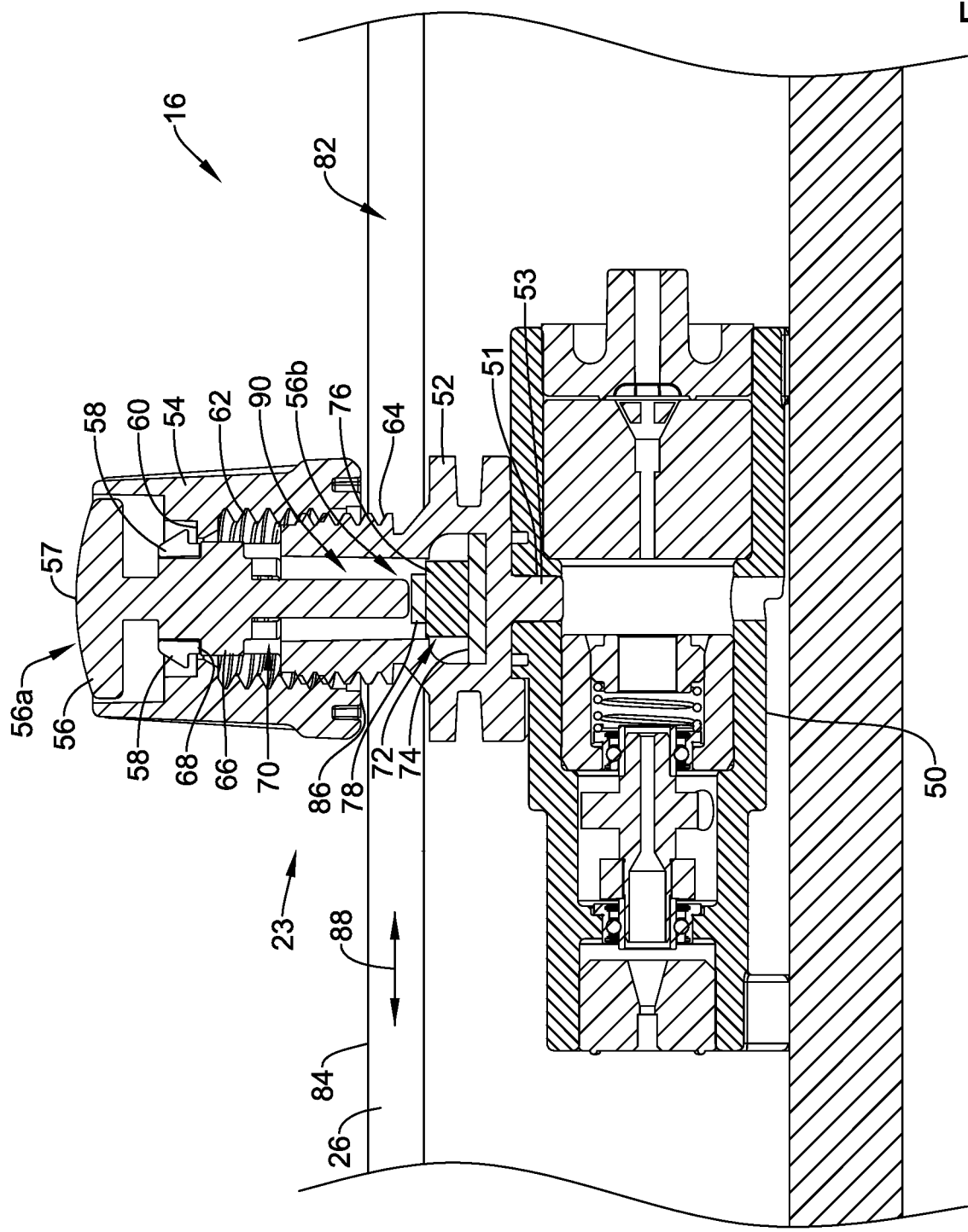
FIG. 5 is a schematic cross-section view of a portion of an example advancer assembly.

The second connection may be configured to facilitate releasably fixing the knob assembly at a position along a predetermined path (e.g., a fixed or adjustable longitudinal path) over which the knob assembly 23 may be configured to translate (e.g., longitudinally translate) to adjust an axial position of the drive mechanism, drive shaft 18, and/or rotational device 20. In some cases, the second connection may be a threaded connection between the knob body 54 and the slide adaptor 52 or other connection configured to adjust for selectively fixing the knob assembly 23 at a position along a predetermined path. When the second connection is a threaded connection, threads on knob body 54 (e.g., inner threads 62 as shown in FIG. 5 or other threads) may engage threads on the slide adaptor 52 (e.g., outer threads 64 as shown in FIGS. 2, 4, and 5 or other threads).

The actuator 56 may be inserted through a central opening or other opening of the knob body 54 and/or the slide adaptor 52. The actuator 56 may be secured in the knob assembly 23 (e.g., at least partially within the openings extending within the knob body 54 and the slide adaptor 52) in a suitable manner. In some cases, the actuator 56 may be secured in the knob assembly 23 such that it may be adjusted or actuated by interacting with a first end 56a of the actuator 56 (e.g., by pressing on a surface at the first end 56a) to allow a second end 56b of the actuator 56 to engage a switch or other electrical or electromechanical component.

Figure 3:
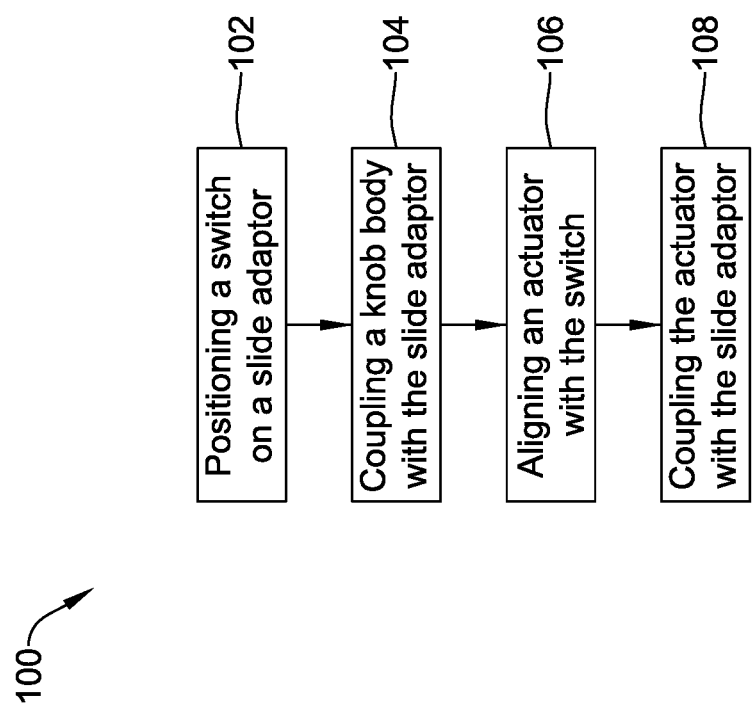
FIG. 3 is a schematic flow diagram of an example method of assembling a knob assembly.

The actuator 56 may be secured relative to the knob body 54 and/or the slide adaptor 52 by engaging one or both of the knob body 54 and the slide adaptor 52. As shown in FIG. 3, the actuator 56 may include a protrusion 66 configured to engage the engagement element 58 (e.g., engage a catch 68 or other feature of the engagement element 58) of the slide adaptor 52 and slide within an opening 70 in the slide adaptor 52 (e.g., in some cases, the opening 70 may be an opening between engagement elements 58). Alternatively or in addition, one or more both of the actuator 56 and the slide adaptor 52 may include an indent or opening for engaging a protrusion of the other one of actuator 56 and the slide adaptor 52.

The knob assembly 23 may include a switch 72, as shown in FIG. 2, configured to initiate a mode of operation of the drive mechanism. In some cases, the switch 72 may be mechanically affixed and in electrical communication with a switch printed circuit board (PCB) 74 to form a switch assembly. The switch 72 may be mechanically affixed and/or in electrical communication with the switch PCB 74 in any suitable manner. In some cases, the switch 72 may be mechanically affixed and/or electrically connected to the switch PCB 74 through one or more connection mechanisms including, but not limited to, solder, adhesive, welding, wire bonds, etc. Alternatively or in addition, the switch assembly may take on one or more other configurations, one or more additional or alternative electrical components, and/or one or more additional or alternative mechanical components.

Although it is not shown in the FIGS., the switch 72 and/or the switch PCB 74 may be in electrical communication with (e.g., electrically connected to and/or in other suitable electrical communication with) a main PCB of the drive assembly 12 for sending electrical signals to the main PCB and/or drive mechanism controller that are configured to adjust a mode of the drive mechanism. Alternatively or in addition, the switch 72 may be directly electrically connected to the drive mechanism (e.g., when the drive mechanism is an electric motor and/or in other configurations) to adjust a mode of the drive mechanism in response to the switch 72 being actuated by the actuator 56 and/or actuated in other suitable manners.

The switch 72 may have a suitable configuration for adjusting a mode of the drive mechanism in response to be actuated by the actuator 56. In some cases, the switch 72 may include a body 76 and a button 78. The button 78 may be configured to translate relative to the body 76 in response to being actuated. For example, when the switch 72 is positioned within the knob assembly 23, the second end 56b of the actuator 56 may interact with the button 78 of the switch 72 to initiate adjusting a mode of the drive mechanism.

The switch 72 may operate in any suitable manner for adjusting a mode of the drive mechanism. In one example, the switch 72 may send a pulse to a drive mechanism controller (not shown) each time the actuator 56 interacts with the switch. The drive mechanism controller may then either initiate placing the drive mechanism to an on mode when a pulse is received and the drive mechanism was in an off mode at the time of receiving the pulse or initiate placing the drive mechanism to an off mode when a pulse is received and the drive mechanism was in an on mode at the time of receiving the pulse. Alternatively or in addition, the switch 72 may operate in a different manner and may be configured to facilitate adjusting one or more other control parameters of the drive mechanism in response to being actuated by the actuator 56. Further, although the switch 72 is described herein as sending pulses to a drive mechanism controller, the switch 72 may take one or more other suitable actions or provide one or more other suitable outputs in response to being actuated by the actuator 56.

When included in the knob assembly 23, the switch 72 may be positioned within the knob assembly 23, such that the second end 56b of the actuator 56 may interact with the switch 72. In one example, the switch 72 may be positioned in a receiving slot 80 of the slide adaptor 52. The switch 72 may be secured within the receiving slot 80 or otherwise secured relative to the slide adaptor 52 though one or more connection mechanisms including, but not limited to, a friction fit in the receiving slot 80, a keyed fit connection, a luer lock connection, a snap fit in the receiving slot 80, adhesive, welding, soldering, a permanent connection, a releasable connection, and/or other suitable connection mechanisms.

FIG. 3 depicts a method 100 of assembling a knob assembly 23 having a slide adaptor (e.g., the slide adaptor 52 or other suitable slide adaptor), a knob body (e.g., the knob body 54 or other suitable knob body), an actuator (e.g., the actuator 56 or other suitable actuator), and a switch (e.g., the switch 72 or other suitable switch). The method 100 may include positioning 102 the switch on the slide adaptor. As discussed above with respect to the switch 72, the switch may be positioned on the slide adaptor in a receiving slot (e.g., the receiving slot 80) or other recess configured to receive the switch and associated components (e.g., the switch PCB 74 and/or other components). Although not necessarily required, the combined slide adaptor and switch may then be coupled with a drive mechanism (e.g., the drive mechanism 50 depicted in FIG. 5 or other suitable drive mechanism) to the extent the slide adaptor is separate from the drive mechanism and the slide adaptor may be positioned within a housing (e.g., the housing 26 or other suitable housing) of an advancer assembly (e.g., the advancer assembly 16 or other suitable advancer assembly). The slide adaptor positioned within the housing of the advancer assembly may be configured to extend through an opening of the housing, but this is not required.

The method 100 may further include coupling 104 the knob body to the slide adaptor. In one example, the knob body may be coupled to the slide adaptor by threading on the knob body engaging threading on the slide adaptor. To further or alternatively couple the knob body to the slide adaptor and prevent or limit separation of the knob body and the slide adaptor, a force may be applied to one or both of the knob body and the slide adaptor to snap or otherwise connect the knob body onto the slide adaptor.

The actuator of the knob assembly may be aligned 106 with the switch to ensure actuation of the actuator will cause actuation of the switch. In some cases, the actuator may be aligned with the switch by inserting the actuator through openings extending through the knob body and/or the slide adaptor. Once aligned with the switch, the actuator may be coupled 108 with the slide adaptor. In some cases, a force may be applied to one or both of the knob body and the slide adaptor to snap or otherwise connect the knob body onto the slide adaptor. When the knob assembly is positioned relative to the housing and assembled, a user may interact with the knob assembly to longitudinally translate an axial position of the drive mechanism, a drive shaft (e.g., the drive shaft 18 or other suitable drive shaft) coupled to the drive mechanism, and/or a rotational device (e.g., the rotational device 20 or other suitable rotational device) coupled to the drive shaft, and fix the drive mechanism, the drive shaft, and/or the rotational device at a position relative to the housing of the advancer assembly, while allowing for adjustment of a mode of the drive mechanism through actuation of the actuator.

FIG. 4 depicts a schematic perspective view of the advancer assembly 16 with a partially exploded view of the knob assembly 23 positioned within and extending through the housing 26, where part of the advancer assembly 16 is cut-away. As shown in FIG. 4, the slide adaptor 52 may extend through an opening 82 in the housing 26. After positioning the slide adaptor 52 in the housing 26 and extending the slide adaptor 52 through the opening 82, the knob body 54 and/or the actuator 56 may be coupled to each other and/or the slide adaptor 52, as discussed herein (e.g., see steps 104, 106, and 108 of the method 100) or in one or more other manners. Although the slide adaptor 52 described herein may be configured to extend through the opening 82, it is conceived that the knob body 54 and/or the actuator 56 may extend through the opening 82 and coupled to the slide adaptor 52 at a location within the housing 26 and/or the knob assembly 23 may take on one or more other configurations configured to perform the functions of the knob assembly 23 described herein.

The opening 82 of the housing 26 may have a suitable configuration for longitudinally translating the drive mechanism, the drive shaft 18, and/or the rotational device 20. As shown in FIG. 4, the opening 82 has an elongated shape and is configured to allow the knob assembly 23 to longitudinally translate along a predetermined path (e.g., a predetermined fixed path or other path). However, the opening 82 may take on one or more other suitable configurations, as desired.

In some cases, the housing 26 of the advancer assembly 16 may include indicia on an outer surface 84 of the housing 26. As depicted in FIG. 4, the indicia, when included, may be positioned at predetermined and/or consistent locations along the opening 82 to provide a user (e.g., a physician or other user) with a measurement or other indication of an axial position of the drive mechanism, the drive shaft 18, and/or the rotational device 20. The indicia may be general tick marks, measurements (e.g., millimeters, centimeters, inches, etc.), and/or other suitable indicia that facilitate providing an understanding of a relative position of the knob assembly 23 and/or the drive mechanism along the opening 82. Alternatively or in addition, other indicia may be provided on the outer surface 84 of the housing 26.

FIG. 5 is a schematic cross-sectional view of a portion of the advancer assembly 16. FIG. 5 depicts the knob assembly 23 coupled to a drive mechanism 50. The depicted drive mechanism 50 is a pneumatic turbine, however, the drive mechanism may be a different pneumatic motor, may be an electric motor, and/or may include one or more other suitable drive mechanisms.

The knob assembly 23 may be coupled to the drive mechanism 50 in a suitable manner that facilitates movement of the drive mechanism 50 in response to movement of the knob assembly 23. For example, the knob assembly 23 may be coupled to the drive mechanism 50 with a friction fit connection, a keyed fit connection, a snap fit connection, a threaded connection, a luer lock connection, an adhesive connection, a weld connection, a solder connection, a permanent connection, a releasable connection, and/or one or more other suitable types of connection. As shown in FIG. 5, an extension 53 of the slide adaptor 52 may extend into a recess 51 of the drive mechanism 50 to form a keyed fit connection between the knob assembly 23 and the drive mechanism 50 that may result in movement (e.g., movement along a central axis) of the drive mechanism 50 in response to movement (e.g., longitudinal movement) of the knob assembly 23.

As can be seen in FIG. 5, the inner threads 62 of the knob body 54 may engage the outer threads 64 of the slide adaptor 52. As such, the knob body 54 may be rotationally adjusted in a first direction to a first position to create a space between a bottom surface 86 of the knob body 54 and the outer surface 84 to allow translation of the knob assembly 23 along the predetermined path at least partially defined by the opening 82 in the housing 26 of the advancer assembly 16, as indicated by arrows 88. If it is desired to fix the knob assembly 23 and/or the drive mechanism 50 at a position along the opening 82, the knob body 54 may be rotated in a second direction to a second position to bring the bottom surface 86 of the knob body 54 into contact with the outer surface 84 of the housing 26 and create a friction fit coupling between the knob body 54 and the housing 26 and prevent or limit longitudinal movement of the knob assembly 23, drive mechanism 50, drive shaft 18, and/or the rotational device 20 relative to the housing 26. Although the knob body 54 may be rotated to adjust an axial position of the knob body 54 relative to the slide adaptor 52 and/or the outer surface 84 of the housing 26, the engagement elements 58 of the slide adaptor 52 may be configured to engage with the shoulder 60 of the knob body 54 to limit separation of the knob body 54 from the housing 26 and/or the slide adaptor 52.

As shown in FIG. 5, the actuator 56 may extend through the knob body 54, through an opening 90 (e.g., a central opening or other opening) extending at least partially through the slide adaptor 52, and align with the switch 72 (e.g., the second end 56b of the actuator 56 may align with the button 78 of the switch 72). In such a configuration, the actuator 56 may be configured to axially translate and engage the button 78 to send signal for adjusting a mode of operation of the drive mechanism. In one example, the first end 56a of the actuator 56 may extend out of the knob body 54 or may otherwise be accessible for actuation from exterior the knob body 54 such that a user may interact with the first end 56a of the actuator 56 to actuate the actuator 56 (e.g., longitudinally translate) such that the second end 56b of the actuator 56 engages the button 78 to actuate the switch 72.

As shown in FIG. 5, the protrusions 66 of the actuator 56 may be received in the opening(s) 70 of the slide adaptor 52. The opening(s) 70 of the slide adaptor 52 and/or the protrusions 66 of the slide adaptor 52 may be configured to allow and/or limit axial movement of the actuator 56 with respect to the slide adaptor 52 due to engagement between the protrusions 66 and the catch 68 of the slide adaptor 52.

Figure 6:
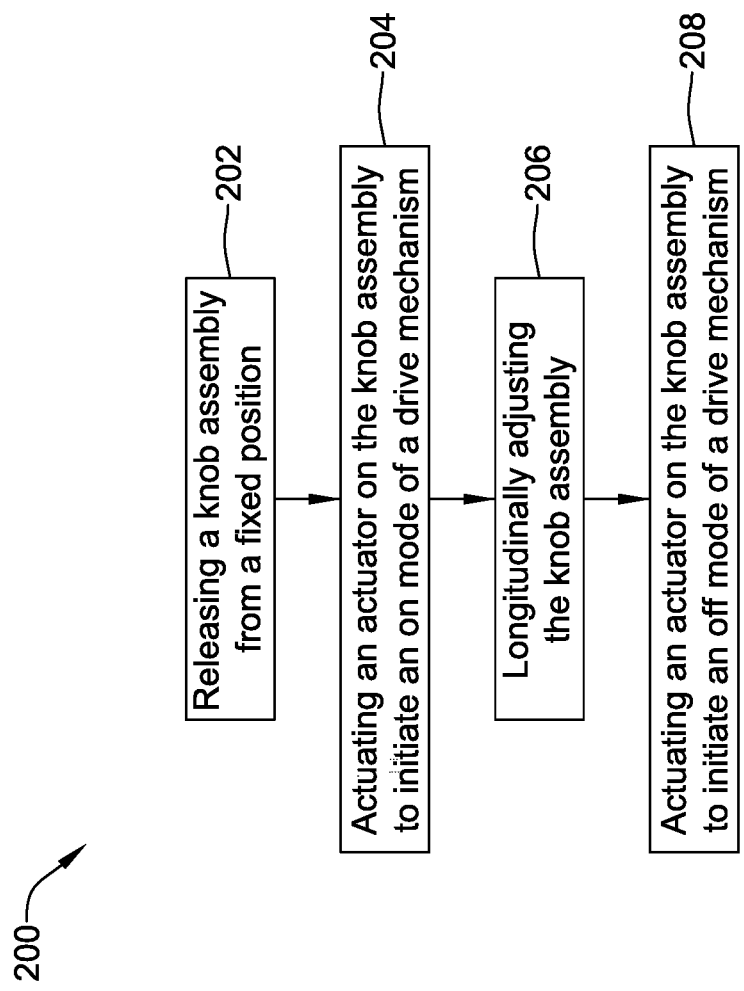
FIG. 6 is a schematic flow diagram of an example method of using an atherectomy system.

FIG. 6 depicts a method 200 of operating a drive assembly 12 of an atherectomy system 10 to pass through an occlusion in a patient's vasculature. The method 200 may include releasing 202 a knob assembly (e.g., the knob assembly 23 or other suitable knob assembly) from a first position (e.g., a fixed position) relative to a housing (e.g., the housing 26 of the advancer assembly or other suitable housing). The knob assembly may be released from a fixed position by rotating a knob body (e.g., the knob body 54 or other suitable knob body) relative to a slide adaptor (e.g., the slide adaptor 52 or other suitable slide adaptor) to a second position (e.g., a released position) that facilitates longitudinal translation of a drive mechanism (e.g., the drive mechanism 50 or other suitable drive mechanism). Alternatively or in addition, the knob assembly may be released from a fixed position relative to the housing in one or more other suitable manners.

When in a released position (as shown in the method 200 of FIG. 5) or a fixed position, an actuator (e.g., the actuator 56 or other suitable actuator) may be actuated 204 to initiate an on mode, an off mode, and/or other mode of the drive mechanism. As discussed above, actuating the actuator may cause engagement with and/or actuation of a switch that results in sending a signal to a drive mechanism controller to change or adjust a mode of the drive mechanism. In one example, if the drive mechanism is in an off mode, actuation of the actuator may initiate the drive mechanism entering an on mode. Similarly, if the drive mechanism is in an on mode, actuation of the actuator may initiate the drive mechanism entering an off mode.

With the drive mechanism in an on mode as a result of actuating the actuator (as shown in the method 200 of FIG. 5), when the drive mechanism is in the off mode, or before the actuator is actuated and while the knob assembly is in a released position, the knob assembly may be longitudinally adjusted 206 (e.g., advanced or retracted). In some cases, a rotational device (e.g., the rotational device 20 or other suitable rotational device) coupled to a drive shaft (e.g., the drive shaft 18 or other suitable drive shaft) may be advanced through a patient's vasculature to an occlusion while the drive mechanism is in the off mode and then the drive mechanism may be actuated to an on mode when the rotational device is adjacent the occlusion. After initiating the on mode of the drive mechanism, the knob assembly may be advanced 206 such that the rotational device may engage the occlusion and bore through the occlusion. Once the occlusion has been passed, the actuator may be actuated 208 a second time to initiate entering the drive mechanism to an off mode. Once the procedure has been performed, the knob assembly may be rotationally adjusted to fix the knob assembly at a position relative to the housing and the rotational device and the drive shaft may be removed from the patient's vasculature with the drive mechanism in the off mode. Alternatively or in addition, one or more of the steps of the method 200 may be repeated as needed to facilitate passing the occlusion in the patient's vasculature.

Although not necessarily depicted in the FIGS., the methods described herein (e.g., methods 100, 200, and/or other methods) may include one or more steps other than those steps described herein and/or the described steps may be performed in one or more other orders, as desired unless an expressly indicated otherwise. Moreover, the methods described herein may be repeated during operation of the atherectomy system 10 upon request or initiation, continuously, continuously at predetermined intervals, and/or at other times.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. An atherectomy device, comprising:
 a housing;
 a drive mechanism positioned within the housing and configured to couple to an elongate member and rotate the elongate member upon actuation;
 a knob assembly in communication with the drive mechanism and operably accessible from exterior the housing, the knob assembly comprises:
  a slide adaptor coupled to the drive mechanism;
  an actuator configured to be actuated to selectively adjust the drive mechanism between an on mode and an off mode;
  a knob body coupled to the slide adaptor and the actuator, the knob body is configured to:
   releasably engage the housing to fix the drive mechanism at an axial location along the housing, and
   rotate relative to the slide adaptor and the actuator; and
 wherein the knob assembly is configured to longitudinally translate to adjust an axial position of the drive mechanism.

2. The device of claim 1, wherein the knob assembly is configured to:
 longitudinally translate along a fixed longitudinal distance; and
 releasably engage the housing to fix the drive mechanism at a location along the fixed longitudinal distance.

3. The device of claim 1, wherein the actuator that is actuated relative to the knob body to selectively adjust the drive mechanism between the on mode and the off mode.

4. The device of claim 1, wherein the knob assembly comprises:
 a switch configured to facilitate adjusting the drive mechanism between the on mode and the off mode; and
 the actuator is configured to engage the switch in response to being actuated, the actuator engages the switch to adjust the drive mechanism between the on mode and the off mode.

5. The device of claim 1, wherein the
 actuator is configured to be actuated relative to the slide adaptor and the knob body to selectively adjust the drive mechanism between the on mode and the off mode.

6. The device of claim 1, wherein the knob assembly comprises:
 a switch configured to axially translate with the drive mechanism and facilitate adjusting the drive mechanism between the on mode and the off mode; and
 wherein the actuator is configured to engage the switch in response to being actuated.

7. The device of claim 6, wherein the knob assembly comprises a printed circuit board in electrical communication with the switch and coupled with the slide adaptor.

8. The device of claim 6, further comprising:
 a control assembly configured to control power to the drive mechanism;
 wherein the knob assembly comprises a printed circuit board in electrical communication with the switch and configured to axially translate with the drive mechanism, the printed circuit board is in electrical communication with the control assembly.

9. The device of claim 1, wherein the actuator is coupled to the slide adaptor and configured to translate with the drive mechanism between a first axial position of the drive mechanism and a second axial position of the drive mechanism.

10. The device of claim 1, wherein the knob body is coupled to the slide adaptor exterior of the housing via a first connection type and a second connection type, the knob body is configured to be adjusted via the second connection to selectively engage the housing and fix the drive mechanism at the axial location along the housing.

11. The device of claim 1, wherein the drive mechanism is a turbine.

12. A method of actuating an atherectomy device of an atherectomy system, the method comprising:
   releasing a knob assembly from a releasably fixed position at a location on a predetermined path along a housing of the atherectomy device, releasing the knob assembly includes adjusting a knob body of the knob assembly relative to an actuator of the knob assembly;
   actuating the actuator of the knob assembly to initiate an on mode of a drive mechanism in the housing of the atherectomy device; and
   longitudinally translating the knob assembly on the predetermined path.

13. The method of claim 12, further comprising:
   when the drive mechanism is in the on mode, actuating the actuator of the knob assembly to initiate an off mode of the drive mechanism.

14. The method of claim 12, wherein the actuator is actuated relative to the knob body while the knob assembly is fixed at the location on the predetermined path.

15. The method of claim 12, wherein the actuator is actuated relative to the knob body while the knob assembly is released from the releasably fixed position.

16. The method of claim 12, further comprising:
   rotating the knob body relative to the actuator until the knob body engages the housing of the atherectomy device to releasably fix the knob assembly relative to the housing.

17. An atherectomy device comprising:
   a drive mechanism configured to rotate an elongate member securable to the drive mechanism;
   a knob assembly comprising:
      a slide adaptor secured relative to the drive mechanism;
      a knob body adjustably secured to the slide adaptor via a first connection type and a second connection type; and
      an actuator adjustably secured to the slide adaptor, the actuator is adjustable along an axis relative to the knob body and the slide adaptor; and
   wherein the knob assembly is configured to longitudinally translate with the drive mechanism and actuation of the actuator initiates a mode of the drive mechanism.

18. The device of claim 17, wherein the knob assembly comprises:
   a switch in communication with the actuator such that actuation of the actuator adjusts the switch to initiate a mode of the drive mechanism.

19. The device of claim 18, wherein the knob assembly comprises:
   a printed circuit board coupled to the slide adaptor and in electrical communication with the switch.

20. The device of claim 17, wherein:
   the knob body is adjustable between a first position that facilitates longitudinal translation of the drive mechanism and a second position that releasably fixes the drive mechanism at a longitudinal location; and
   the actuator is actuatable to initiate a mode of the drive mechanism when the knob body is in the first position and when the knob body is in the second position.

* * * * *